United States Patent
Lee et al.

(10) Patent No.: US 7,359,744 B2
(45) Date of Patent: Apr. 15, 2008

(54) BODY SURFACE BIO-POTENTIAL SENSOR HAVING MULTIPLE ELECTRODES AND APPARATUS INCLUDING THE SAME

(75) Inventors: Jeong-hwan Lee, Suwon-si (KR); Jin-sang Whang, Suwon-si (KR); Kun-soo Shin, Seongnam-si (KR); Kyung-ho Kim, Yongin-si (KR); Hyung-sok Yeo, Yongin-si (KR)

(73) Assignee: Samsung Eectronics Co., Ltd., Suwon-si, Gyeonggi-do (KR)

( * ) Notice: Subject to any disclaimer, the term of this patent is extended or adjusted under 35 U.S.C. 154(b) by 406 days.

(21) Appl. No.: 11/030,973

(22) Filed: Jan. 10, 2005

(65) Prior Publication Data
US 2005/0154273 A1    Jul. 14, 2005

(30) Foreign Application Priority Data
Jan. 8, 2004    (KR) .................... 10-2004-0001097

(51) Int. Cl.
*A61B 5/04*    (2006.01)
(52) U.S. Cl. .................. 600/392; 600/391; 600/393
(58) Field of Classification Search ................ 600/393
See application file for complete search history.

(56) References Cited

U.S. PATENT DOCUMENTS

| | | | |
|---|---|---|---|
| 4,899,753 A | 2/1990 | Inoue et al. | |
| 4,947,846 A * | 8/1990 | Kitagawa et al. | 600/391 |
| 4,969,468 A | 11/1990 | Byers et al. | |
| 6,201,981 B1 | 3/2001 | Yarita | 600/372 |
| 6,238,338 B1 | 5/2001 | DeLuca et al. | |
| 6,267,723 B1 | 7/2001 | Matsumura et al. | 600/300 |
| 6,577,893 B1 | 6/2003 | Besson et al. | |
| 6,622,035 B1 | 9/2003 | Merilainen et al. | |
| 6,690,959 B2 * | 2/2004 | Thompson | 600/372 |
| 6,775,566 B2 * | 8/2004 | Nissila | 600/382 |
| 6,961,603 B2 * | 11/2005 | Merilainen | 600/383 |
| 2002/0028991 A1 | 3/2002 | Thompson | |
| 2002/0045836 A1* | 4/2002 | Alkawwas | 600/509 |

FOREIGN PATENT DOCUMENTS

| | | |
|---|---|---|
| EP | 1 060 704 | 12/2000 |
| EP | 1 488 740 | 12/2004 |

* cited by examiner

*Primary Examiner*—Lee S. Cohen
(74) *Attorney, Agent, or Firm*—Lee & Morse, P.C.

(57) ABSTRACT

In a body surface bio-potential sensor, and an apparatus for detecting biomedical signals having the same, the body surface bio-potential sensor includes a flexible membrane having a wire layer, a plurality of electrodes attached on a first surface of the membrane at predetermined intervals, each of the plurality of electrodes having a plurality of needles on a surface thereof, each of the plurality of needles having a predetermined height, and a cohesive layer covering the first surface of the membrane, the cohesive layer exposing regions of the flexible membrane corresponding to positions of the plurality of electrodes.

20 Claims, 4 Drawing Sheets

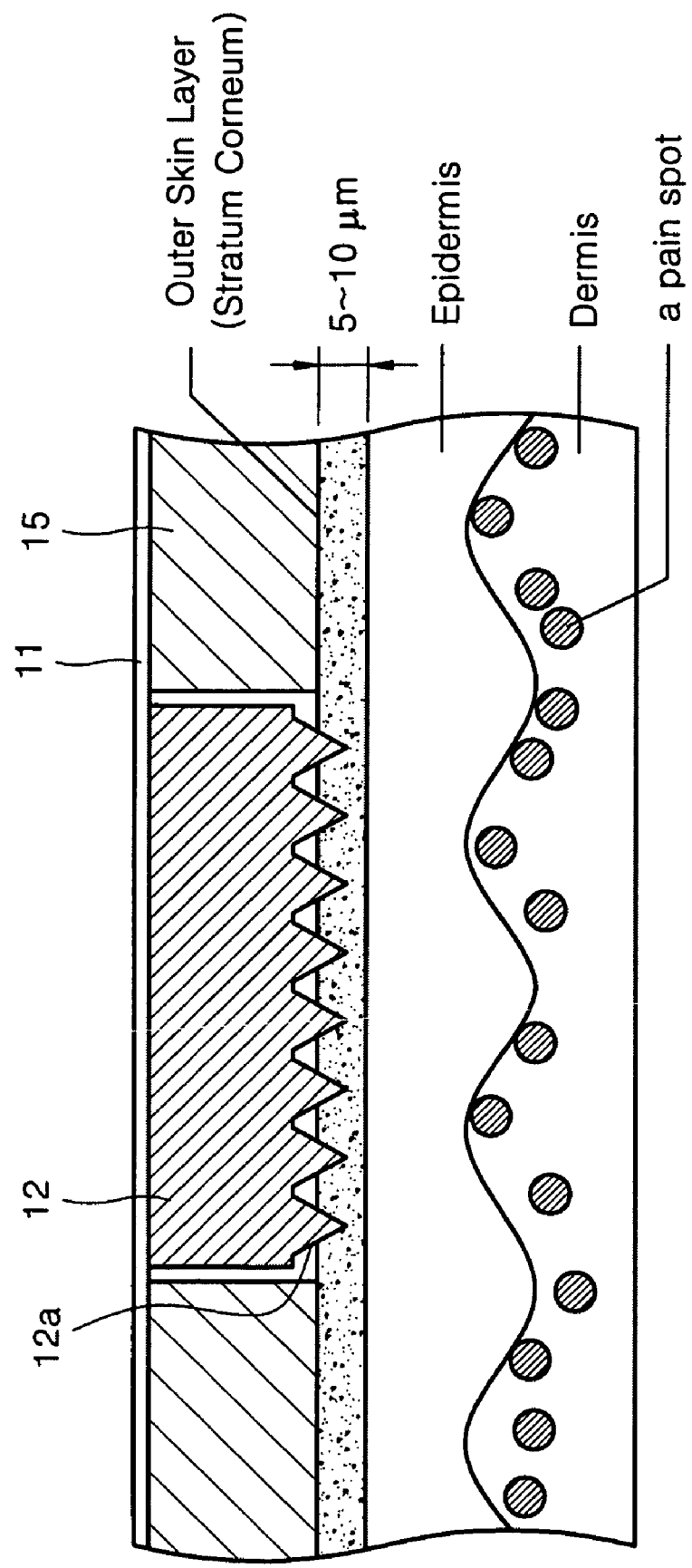

BODY SURFACE BIO-POTENTIAL SENSOR HAVING MULTIPLE ELECTRODES AND APPARATUS INCLUDING THE SAME

BACKGROUND OF THE INVENTION

1. Field of the Invention

The present invention relates to a body surface bio-potential sensor having multiple electrodes and an apparatus including the same.

2. Description of the Related Art

Conventional biomedical signal sensors use a pad provided with one or more electrodes, in which the electrodes are connected to a signal processing unit by separate lead wires. Each electrode has a snap connected to a terminal of the lead wires. Such a connection configuration, however, may disadvantageously generate abnormal noise caused by friction between the snap and the terminal of the lead wires when a person being examined moves. The abnormal noise may reduce the accuracy of detection of the biomedical signals. Furthermore, the lead wires connecting the signal processing unit to the electrodes may limit the movement of the person being examined, and, more importantly, may hinder administration of first-aid treatment during an emergency.

In an effort to overcome the above disadvantage, a gel material may be spread on a conventional electrode to promote a smooth electrical contact considering a high resistance characteristic of human skin. The gel material, however, causes an uncomfortable sensation and, in some cases, may cause irritation to the skin.

Conventional methods of connecting an electrode to lead wires and of reducing a noise level have been proposed in an attempt to overcome the above disadvantages. In one such conventional method, a detection unit is also connected by the lead wires. Disadvantageously in this method, however, movement of an examiner, as well as a person to be examined, are inevitably limited.

Another conventional method using a transmitter has tried to eliminate inconveniences caused by the lead wires. However, use of a gel material should still be used to contact an electrode to human skin.

SUMMARY OF THE INVENTION

The present invention is therefore directed to a body surface bio-potential sensor having multiple electrodes and an apparatus including the same, which substantially overcome one or more of the problems due to the limitations and disadvantages of the related art.

It is a feature of an embodiment of the present invention to provide a body surface bio-potential sensor having multiple electrodes and an apparatus including the same that provide a sensor for detecting biomedical signals and a biomedical signal detection system having the same, by which biomedical signals can be stably detected from a person being examined without use of a gel material.

At least one of the above features and other advantages may be provided by a body surface bio-potential sensor including a flexible membrane having a wire layer, a plurality of electrodes attached on a first surface of the membrane at predetermined intervals, each of the plurality of electrodes having a plurality of needles on a surface thereof, each of the plurality of needles having a predetermined height, and a cohesive layer covering the first surface of the membrane, the cohesive layer exposing regions of the flexible membrane corresponding to positions of the plurality of electrodes.

The predetermined height of each of the plurality of needles may be about 5 µm or less.

The sensor may further include a terminal for outputting electrical signals to an external unit, the terminal being provided on a second surface of the membrane, the second surface being opposite to the first surface, and being electrically connected to the plurality of electrodes.

The sensor may further include a terminal for outputting electrical signals to an external unit, the terminal being provided on a second surface of the membrane, the second surface being opposite to the first surface, and being electrically connected to the plurality of electrodes.

The flexible membrane may include a magnetic structure for connecting the flexible membrane to a predetermined unit for processing signals from the plurality of electrodes. The magnetic structure may be a plurality of magnets.

The sensor may further include a release base film on the cohesive sheet.

At least one of the above features and other advantages may be provided by an apparatus for detecting biomedical signals including a membrane, a sensor formed on the membrane, and a transmitter removably attached to the sensor to transmit electrical signals from a sensor as radio signals, wherein the sensor includes a flexible membrane having a wire layer, a plurality of electrodes attached on a first surface of the membrane at predetermined intervals, each of the plurality of electrodes having a plurality of needles on a surface thereof, each of the plurality of needles having a predetermined height, and a cohesive layer covering the first surface of the membrane, the cohesive layer exposing regions of the flexible membrane corresponding to positions of the plurality of electrodes.

The predetermined height of each of the plurality of needles may be about 5 µm or less.

The membrane and the transmitter may each include a terminal, the terminals having complementary structures and being operable to deliver biomedical signals from the plurality of electrodes.

The membrane and the transmitter may include a magnetic structure for providing a removable attaching structure. The magnetic structure may be a plurality of magnets.

The apparatus may further include a release base film on the cohesive sheet.

BRIEF DESCRIPTION OF THE DRAWINGS

The above and other features and advantages of the present invention will become more apparent to those of ordinary skill in the art by describing in detail exemplary embodiments thereof with reference to the attached drawings in which:

FIG. 4 illustrates a partially enlarged cross-sectional view of the sensor shown in FIG. 1 engaging a region of skin.

DETAILED DESCRIPTION OF THE INVENTION

Figure 1:
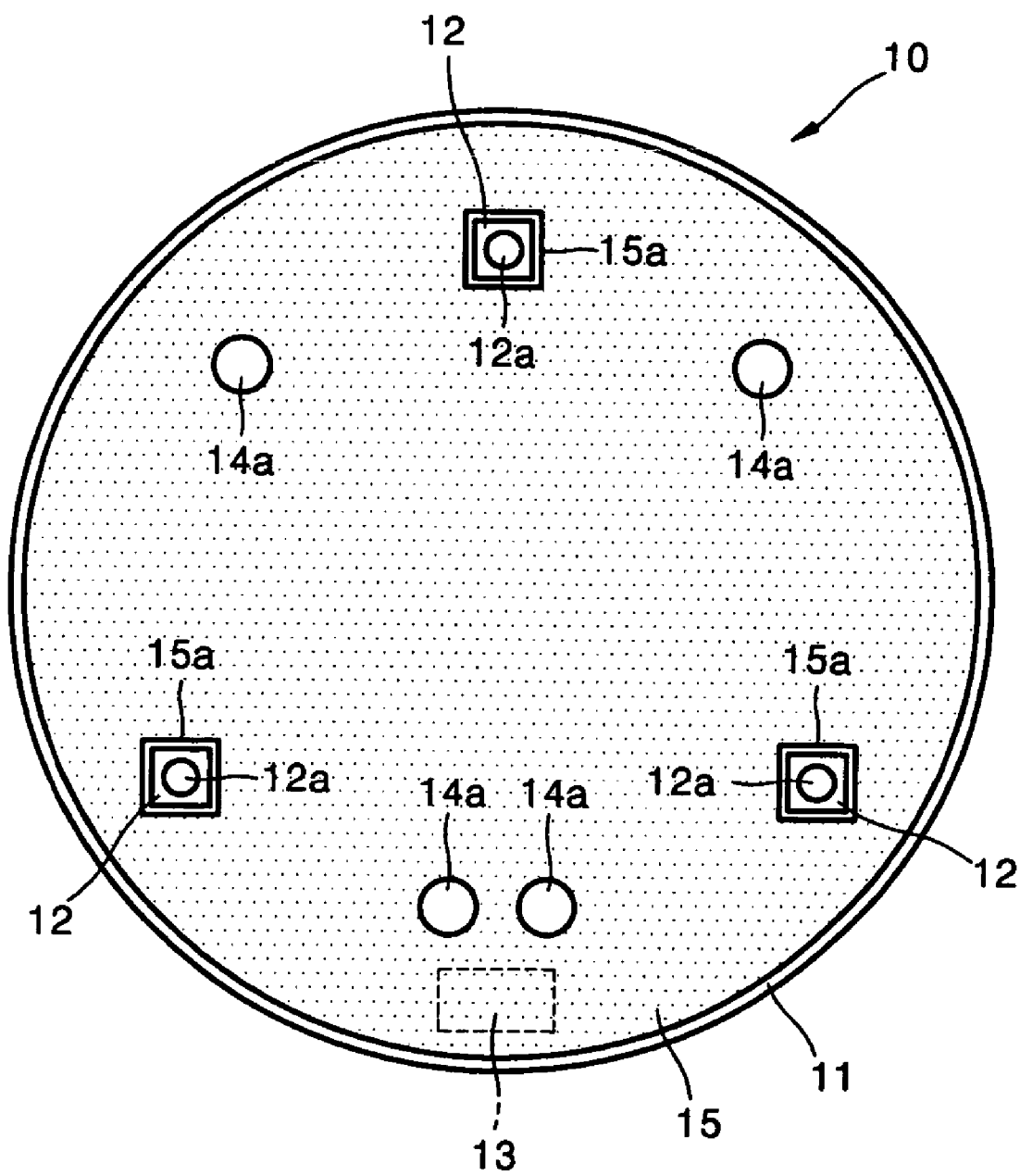
FIG. 1 illustrates a plan view of a sensor according to an embodiment of the present invention.

Korean Patent Application No. 10-2004-0001097, filed on Jan. 8, 2004, in the Korean Intellectual Property Office, and entitled: "Body Surface Bio-Potential Sensor Having Multiple Electrodes and Apparatus Having the Body Surface Bio-Potential Sensor," is incorporated by reference herein in its entirety.

The present invention will now be described more fully with reference to the accompanying drawings, in which exemplary embodiments of the invention are shown. The invention may, however, be embodied in many different forms and should not be construed as being limited to the embodiments set forth herein. Rather, these embodiments are provided so that this disclosure will be thorough and complete, and will fully convey the concept of the invention to those skilled in the art. Like reference numerals indicate like elements throughout.

Figure 2:
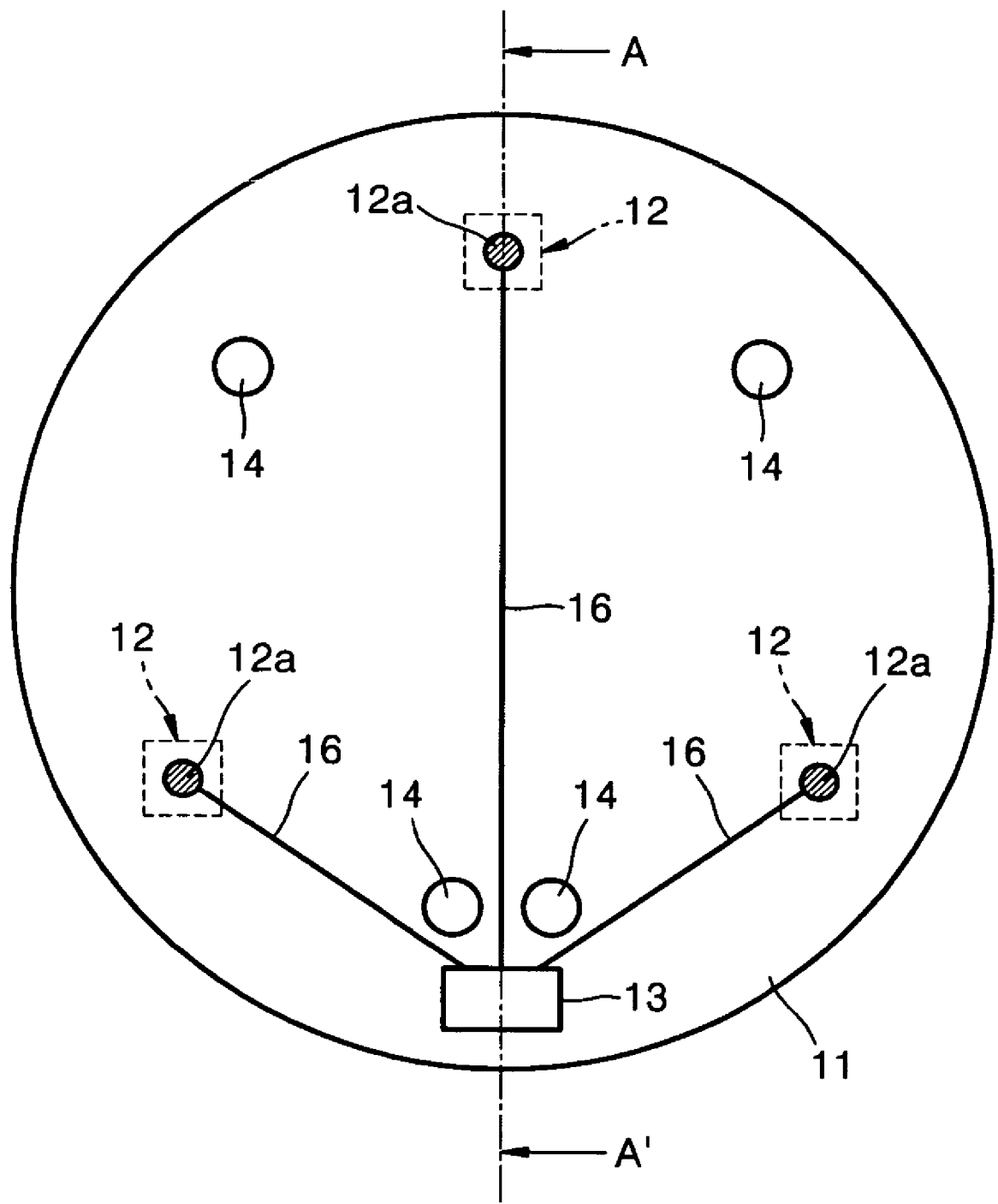
FIG. 2 illustrates a bottom view of the sensor shown in FIG. 1.
Figure 3:
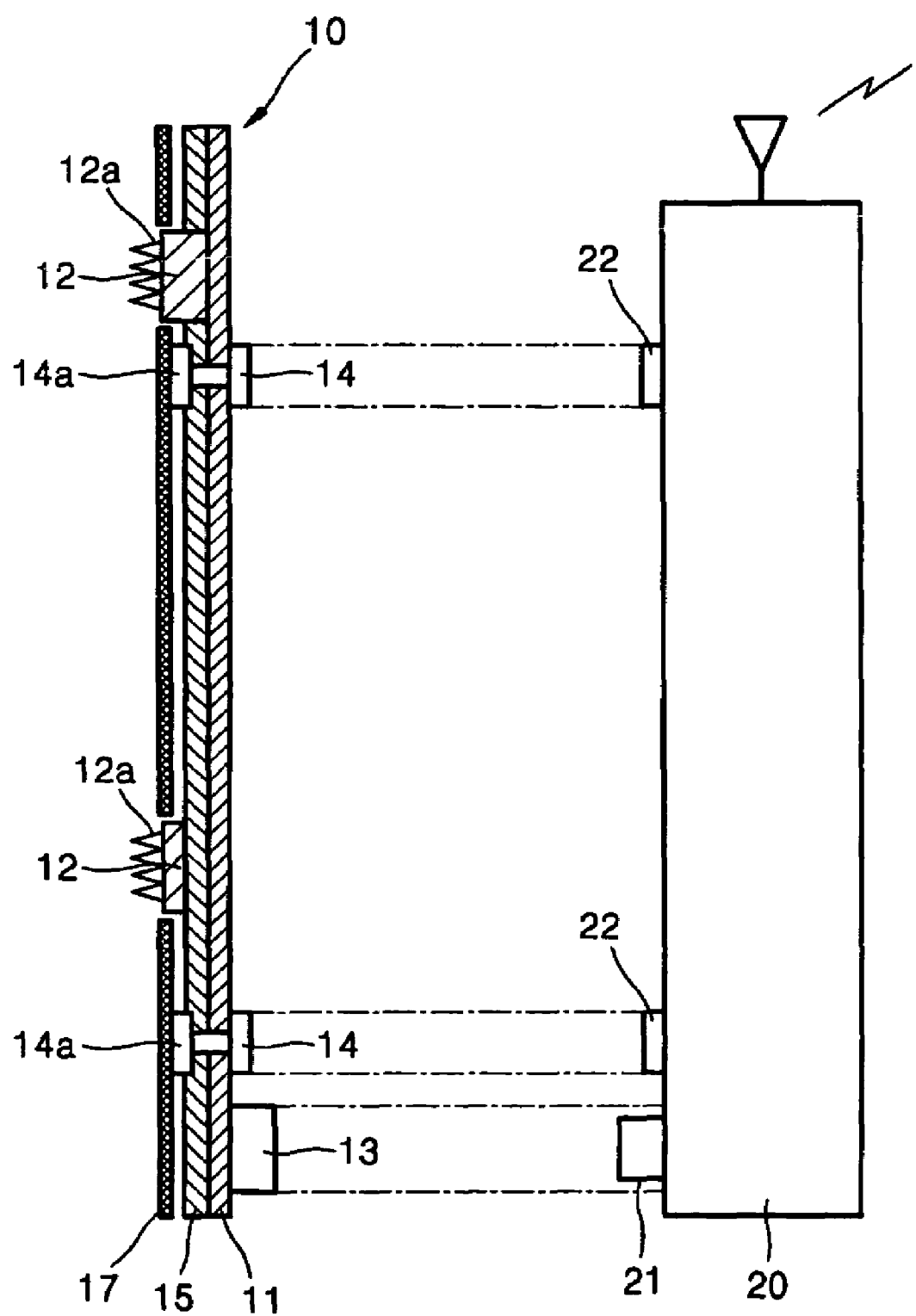
FIG. 3 illustrates a cross-sectional view taken along line A-A' of FIG. 2 along with an external unit.

FIG. 1 illustrates a plan view of a sensor according to an embodiment of the present invention. FIG. 2 illustrates a bottom view of the sensor shown in FIG. 1. FIG. 3 illustrates a cross-sectional view taken along a line A-A' of FIG. 2 and an external unit.

Referring to FIGS. 1 through 3, a sensor 10 uses a disk-shaped membrane 11, which is a flexible printed circuit board (PCB) having a wire layer 16 formed thereon, as a substrate. The membrane 11 has a plurality of electrodes 12 attached to a first side thereof and a plurality of magnets 14 attached to a second side thereof, which is opposite to the first side. In the present embodiment, an exemplary three electrodes 12 are arranged in a triangular configuration. The electrodes 12 are connected to a terminal 13, which is provided near an edge of the membrane 11, through the wire layer 16, which may be formed on either a top or bottom surface of the membrane 11. The terminal 13 may be a connector complementarily paired with another terminal 21 provided on an external unit 20, e.g., a transmitter, which transmits electrical signals as radio signals. The front surface of the membrane 11 is provided with a cohesive sheet 15, which is to be attached to human skin. The cohesive sheet 15 is provided with through holes 15a In positions corresponding to the electrodes 12 and magnets 14. It is noted that the through holes for the magnets 14 are covered by the fixing elements 14a.

Typically, each of the magnets 14 has a button shape and is provided on a back side of the membrane 11 to be fixed with respect to the membrane 11. A plurality of fixing elements 14a, which fix the magnets 14, is provided on an opposite side of the membrane 11. The fixing elements 14a may extend through the cohesive sheet 15 and the membrane 11. In addition, the transmitter 20 is also provided with a plurality of button type permanent magnets 22 each at a position corresponding to one of the plurality of magnets 14 provided on the sensor 10.

According to this configuration, the sensor 10 and the transmitter 20 can be combined with each other using the magnets 14 and 22, which may be permanent magnets. In this case, the two terminals 13 and 21 are interconnected, thereby allowing transmission of electrical signals and supplementing a bonding force between the sensor 10 and the transmitter 20. The sensor 10 may further include a release base film 17 for protecting the cohesive sheet 15.

When the sensor 10 is attached to a subject, the electrodes 12 directly contact human skin without applying a gel material thereto, thereby increasing a signal detection sensitivity. Moreover, the sensor 10 and the transmitter 20 do not require a separate lead wire for connecting them. Therefore, it is possible to reduce mechanical-electrical noise caused by the lead wire.

In addition, it is possible to directly connect a plurality of wires to a part of a human body in order to detect low intensity electrical signals with high efficiency and transmit the signals to units such as an electrocardiograph. Furthermore, an examiner and a person being examined are able to move freely without being hindered by the lead wires.

In conventional methods, a direct unstable contact between the biomedical electrodes and the human skin may generate complex voltages or impedances, thereby limiting an accurate measurement of the electrical signals. To avoid this problem, conventional methods use a conductive hydrogel adhesive to attach the electrodes to the human skin via a conductive polymer medium to obtain stable electrical signals through close adhesion as well as not to avoid harming the human skin. However, such an adhesive solidifies after a predetermined time, so that its function is significantly degraded. To avoid this problem in the embodiment according to the present invention, a plurality of needles 12a may be provided on the electrodes to improve an electrical contact stability. The needles 12a are formed on the surfaces of the electrodes using micro electro-mechanic system (MEMS) technology.

FIG. 4 illustrates a partially enlarged cross-sectional view of one of the electrodes 12 of the sensor 10 shown in FIG. 1 with respect to skin. A plurality of needles 12a is provided on the surfaces of the electrodes 12. Each needle 12a has a height sufficient to pass through the stratum corneum of the skin, but not to reach the epidermis, e.g., about 5 µm or less. This height is selected so the needle 12a does not stimulate the epidermis or dermis, which includes pain spots. More specifically, the needles 12a of the electrode 12 penetrated into the skin to a predetermined depth so that the person being examined does not feel pain, while increasing electrical contact sensitivity. Therefore, conventional conductive gels are not necessary in connection with the present invention.

Now, a process for forming the sensor 10 will be briefly described. The membrane 11, which is a flexible film and has the wire layer 16 on a surface thereof, may be produced using a typical flexible printed circuitry (FPC) method. The electrode 12 having the needles 12a may be produced using MEMS technologies such as a micro finger or an electro fine forging. The cohesive sheet 15 may be made of a cohesive polymer, and through holes 15a therein may be made in predetermined positions using a punching machine. The through holes 15a may be provided in predetermined positions relative to the magnets 14 as well as the electrodes 12. The cohesive polymer sheet 15 may be protected by a release base film 17, and one surface thereof may be attached to the membrane 11. Each electrode 12 may be soldered into circuit sections of the membrane 11. A bonding area may be provided at predetermined positions on the membrane 11 to bond the electrodes 12.

In the above embodiment, detailed descriptions have not been provided for the transmitter 20 and the terminal 21 connected thereto. However, these components may be readily provided by one skilled in the art using conventionally known technology.

The sensor 10 according to an embodiment of the present invention includes an easily removable structure from the transmitter 20, does not use wires, and thus has a low noise level. In addition, due to a stable electrical connection structure, no complex voltages or impedances are caused by an unstable contact between the electrodes 12 and the human skin. Particularly, since the sensor 10 has a structure in which a contact between the electrode 12 and human skin can be achieved without using a gel, and the needles 12*a* pass through the stratum corneum, it is possible to obtain accurate biomedical signals.

The present invention is suitable for use in a signal detection apparatus for living bodies, and, particularly, for use in connection with a remote biomedical examination.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A body surface bio-potential sensor, comprising:
   a flexible membrane including a first surface and a second surface opposite the first surface, the flexible membrane includes a wire layer;
   a plurality of electrodes attached on the first surface of the membrane at predetermined intervals, each of the plurality of electrodes having a plurality of needles on a surface thereof, each of the plurality of needles having a predetermined height;
   a cohesive layer covering the first surface of the membrane, the cohesive layer exposing regions of the flexible membrane corresponding to positions of the plurality of electrodes; and
   a plurality of magnets attached on the second surface of the membrane.

2. The sensor as claimed in claim 1, wherein the predetermined height of each of the plurality of needles is about 5 μm or less.

3. The sensor as claimed in claim 2, further comprising a terminal for outputting electrical signals to an external unit, the terminal being provided on the second surface of the membrane, and being electrically connected to the plurality of electrodes.

4. The sensor as claimed in claim 2, wherein the plurality of magnets connect the flexible membrane to an external unit so as to process signals from the plurality of electrodes.

5. The sensor as claimed in claim 1, further comprising a terminal for outputting electrical signals to an external unit, the terminal being provided on the second surface of the membrane, and being electrically connected to the plurality of electrodes.

6. The apparatus as claimed in claim 5, wherein the terminal on the membrane transmits electrical signals to a terminal on the external unit.

7. The apparatus as claimed in claim 6, wherein the external unit is a transmitter.

8. The sensor as claimed in claim 1, wherein the plurality of magnets connect the flexible membrane to an external unit so as to process signals from the plurality of electrodes.

9. The sensor as claimed in claim 1, further comprising a release base film on the cohesive layer.

10. The apparatus as claimed in claim 1, wherein each of the plurality of magnets is covered by a fixing element, the fixing element is on the first surface of the membrane.

11. An apparatus for detecting biomedical signals, comprising:
    a sensor; and
    a transmitter removably attached to the sensor to transmit electrical signals from the sensor as radio signals,
    wherein the sensor includes:
      a flexible membrane including a first surface and a second surface opposite the first surface, the flexible membrane includes a wire layer;
      a plurality of electrodes attached on the first surface of the membrane at predetermined intervals, each of the plurality of electrodes having a plurality of needles on a surface thereof, each of the plurality of needles having a predetermined height;
      a cohesive layer covering the first surface of the membrane, the cohesive layer exposing regions of the flexible membrane corresponding to positions of the plurality of electrodes; and
      a plurality of magnets attached on the second surface of the membrane.

12. The apparatus as claimed in claim 11, wherein the predetermined height of each of the plurality of needles is about 5 μm or less.

13. The apparatus as claimed in claim 12, wherein the membrane and the transmitter each comprise a terminal, the terminals having complementary structures and being operable to deliver biomedical signals from the plurality of electrodes.

14. The apparatus as claimed in claim 13, wherein the terminal of the membrane is provided on the second surface of the membrane.

15. The apparatus as claimed in claim 12, wherein the membrane and the transmitter provide a removable attaching structure.

16. The apparatus as claimed in claim 11, wherein the membrane and the transmitter each comprise a terminal, the terminals having complementary structures and being operable to deliver biomedical signals from the plurality of electrodes.

17. The apparatus as claimed in claim 16, wherein the terminal of the membrane is provided on the second surface of the membrane.

18. The apparatus as claimed in claim 11, wherein the membrane and the transmitter provide a removable attaching structure.

19. The apparatus as claimed in claim 11, further comprising a release base film on the cohesive layer.

20. The apparatus as claimed in claim 11, wherein each of the plurality of magnets is covered by a fixing element, the fixing element is on the first surface of the membrane.

* * * * *